US008933037B2

(12) United States Patent
Kenner et al.

(10) Patent No.: US 8,933,037 B2
(45) Date of Patent: Jan. 13, 2015

(54) METHODS INVOLVING PDGFRBETA INHIBITORS

(75) Inventors: Lukas Kenner, Vienna (AT); Daniela Laimer, Vienna (AT)

(73) Assignee: Medizinische Universitat Wien, Vienna (AT)

( * ) Notice: Subject to any disclaimer, the term of this patent is extended or adjusted under 35 U.S.C. 154(b) by 0 days.

(21) Appl. No.: 13/498,827

(22) PCT Filed: Sep. 28, 2010

(86) PCT No.: PCT/EP2010/064367
§ 371 (c)(1),
(2), (4) Date: Jun. 11, 2012

(87) PCT Pub. No.: WO2011/036305
PCT Pub. Date: Mar. 31, 2011

(65) Prior Publication Data
US 2012/0252736 A1   Oct. 4, 2012

Related U.S. Application Data

(60) Provisional application No. 61/262,526, filed on Nov. 18, 2009.

(30) Foreign Application Priority Data

Sep. 28, 2009   (EP) ..................................... 09171469

(51) Int. Cl.
*A61P 35/00*   (2006.01)
*A61K 31/506*   (2006.01)
*A61K 31/404*   (2006.01)
*A61K 31/4439*   (2006.01)
*A61K 45/06*   (2006.01)

(52) U.S. Cl.
CPC ............. *A61K 31/506* (2013.01); *A61K 31/404* (2013.01); *A61K 31/4439* (2013.01); *A61K 45/06* (2013.01)
USPC .......................................... 514/19.3; 514/275

(58) Field of Classification Search
None
See application file for complete search history.

(56) References Cited

U.S. PATENT DOCUMENTS

| 2005/0119352 | A1 | 6/2005 | Li et al. ........................ 514/681 |
| 2009/0053241 | A1* | 2/2009 | Zhu et al. ................... 424/172.1 |
| 2009/0215835 | A1 | 8/2009 | Wilhelm ....................... 514/350 |

FOREIGN PATENT DOCUMENTS

| WO | WO 2005/075454 | 8/2005 |
| WO | WO 2007/053573 | 5/2007 |
| WO | WO 2008/037716 | 4/2008 |
| WO | WO 2009/065048 | 5/2009 |

OTHER PUBLICATIONS

Metzgeroth et al ("Recurrent finding of the FIP1L1-PDGFRA fusion gene in eosinophilia-associated acute myeloid leukemia and lymphoblastic T-cell lymphoma." Leukemia, 2007; 21:1183-1188).*

(Continued)

*Primary Examiner* — Wu-Cheng Winston Shen
*Assistant Examiner* — Rayna B Rodriguez
(74) *Attorney, Agent, or Firm* — Fulbright & Jaworski LLP

(57) ABSTRACT

The invention refers to PDGFRbeta inhibitor for use in the antiproliferative treatment of T-cell lymphoma, in particular NHL, ALCL and PTCL.

13 Claims, 11 Drawing Sheets

(56) References Cited

OTHER PUBLICATIONS

Thompson et al ("Differential gene expression in anaplastic lymphoma kinase—positive and anaplastic lymphoma kinase—negative anaplastic large cell lymphomas." Human Pathology, 2005; 36:494-504.).*

Dietz et al ("Imatinib mesylate inhibits T-cell proliferation in vitro and delayed-type hypersensitivity in vivo." Blood, 2004; 104(4):1094-1099).*

Imatinib Drug Information (Medline Plus, http://www.nlm.nih.gov/medlineplus/druginfo/meds/ a606018.html, Wayback Machine Archive, Oct. 3, 2008).*

Ergin et al. "Inhibition of tyrosine kinase activity induces caspase-dependent apoptosis in anaplastic large cell lymphoma with NPM-ALK (p80) fusion protein", Experimental Hematology, vol. 29, No. 9, pp. 1082-1090, Sep. 2001.

Galkin et al., "Identification of NVP-TAE684, a potent, selective, and efficacious inhibitor of NPM-ALK", Proceedings of the National Academy of Sciences, vol. 104, pp. 270-275, 2007.

Jacobsen, "Anaplastic Large-Cell Lymphoma, T-/Null-Cell Type", The Oncologist, vol. 11, pp. 831-840, 2006.

Kenner et al., "Mice lacking JunB are osteopenic due to cell-autonomous osteoblast and osteoclast defects", The Journal of Cell Biology, vol. 164, pp. 613-623, 2004.

Laimer et al., "Loss of JunB and cJun in NPM-ALK induced ALCL results in loss of PDGFRSS expression and increased survival advantage", Proceedings of the American Association for Cancer Research Annual Meeting, vol. 50, p. 73, Apr. 2009.

Lansigan et al., "A pilot study of sorafenib examining biomarkers in refractory or relapsed T-cell lymphoma patients", Journal of Clinical Oncology, vol. 28, May 20, 2010.

Mathas et al., "Aberrantly expressed c-Jun and JunB are a hallmark of Hodgkin lymphoma cells, stimulate proliferation and synergize with NF-kB", The European Molecular Biology Organization Journal, vol. 21, pp. 4104-4113, 2002.

Nguyen et al., "Inhibition of MEK/ERK1/2 sensitize lymphoma cells to sorafenib-induced apoptosis", Leukemia Research, vol. 34, pp. 379-386, 2010.

PCT International Search Report issued in International Patent Application No. PCT/EP2010/064367, dated Mar. 14, 2011.

Pullarkat et al., "Megakaryocytic blast crisis as a presenting manifestation of chronic myeloid leukemia", Leukemia Research, vol. 32, pp. 1770-1775, 2008.

Rassidakis et al., "c-kit is not expressed in Hodgkin disease and anaplastic lymphoma kinase (ALK)-positive anaplastic large cell lymphoma", Blood Reviews, vol. 102, pp. 4619-4620, 2003.

Rassidakis et al., "Lack of c-kit (CD117) expression in CD30 + lymphomas and lymphomatoid papulosis", Modern Pathology, vol. 17, pp. 946-953, 2004.

Savage et al., "Peripheral T-Cell Lymphomas", Blood Reviews, Churchill Livingstone, vol. 21, No. 4, pp. 201-216, Jun. 8, 2007.

Schuelper et al., "Preclinical evaluation of sorafenib against B- and T-cell lymphoma", Haematology Meeting Reports, Foundazione Ferrata Storti, IT, vol. 3, No. 1, p. 76, Jan. 1, 2009.

Verbeek et al., "T-cell lymphoproliferative disorder potentially induced by imatinib in a patient with GIST", Nature Reviews: Clinic Oncology, vol. 7, pp. 116-119, 2010.

Watanabe et al., "JunB Induced by Constitutive CD30-Extracellular Single-Regulated Kinase 1/2 Mitogen-Activated protein Kinase Singaling Activates the CD30 Prometer in Anaplastic Large Cell Lymphoma and Reed-Sternberg Cells of Hodgkin Lymphoma", Cancer Research, vol. 65, pp. 7628-7634, 2005.

* cited by examiner

| EMSA sequences | |
|---|---|
| AP15' | CGCTTGATTGACTCAGCCGGAA |
| AP13' | TTCCGGCTGACTCATCAAGCG |
| AP1mut5' | CGCTTGATTGACTCAGCCGGAA |
| AP1mut3' | TTCCGGCCAAGTCATCAAGCG |
| PDGFRBAP15 | TAAAAGTGACTCAGTGGCT |
| PDGFRBAP13 | AGCCACTGACTCACTTTTA |
| PDGFRBAP1mut5 | TAAAAGTGACTTGGTGGCT |
| PDGFRBAP1mut3 | AGCCACCAAGTCACTTTTA |

Imatinib and Nilotinib Treatment in NPM-ALK Cells

Imatinib and Nilotinib Treatment Xenograft Mice

SEQUENCE LISTING

```
<160> NUMBER OF SEQ ID NOS: 24

<210> SEQ ID NO 1
<211> LENGTH: 25
<212> TYPE: DNA
<213> ORGANISM: Homo sapiens

<400> SEQUENCE: 1
gtggtcttaa ggttgaagtg tggtt                                     25

<210> SEQ ID NO 2
<211> LENGTH: 22
<212> TYPE: DNA
<213> ORGANISM: Homo sapiens

<400> SEQUENCE: 2
gcttccggcg gtacactact aa                                        22

<210> SEQ ID NO 3
<211> LENGTH: 17
<212> TYPE: DNA
<213> ORGANISM: Homo sapiens

<400> SEQUENCE: 3
ggctttgcgg acggttt                                              17

<210> SEQ ID NO 4
<211> LENGTH: 19
<212> TYPE: DNA
<213> ORGANISM: Homo sapiens
```

-continued

```
<400> SEQUENCE: 4
ggcgtcacgt ggttcatct                                           19

<210> SEQ ID NO 5
<211> LENGTH: 20
<212> TYPE: DNA
<213> ORGANISM: Homo sapiens

<400> SEQUENCE: 5
tgactgcaaa gatggaaacg                                          20

<210> SEQ ID NO 6
<211> LENGTH: 19
<212> TYPE: DNA
<213> ORGANISM: Homo sapiens

<400> SEQUENCE: 6
gctctcggac tggaggaac                                           19

<210> SEQ ID NO 7
<211> LENGTH: 22
<212> TYPE: DNA
<213> ORGANISM: Homo sapiens

<400> SEQUENCE: 7
tgccagttcc accttgaatg aa                                       22

<210> SEQ ID NO 8
<211> LENGTH: 22
<212> TYPE: DNA
<213> ORGANISM: Homo sapiens

<400> SEQUENCE: 8
agttgtgcct caggctctgc tt                                       22

<210> SEQ ID NO 9
<211> LENGTH: 13
<212> TYPE: DNA
<213> ORGANISM: Mus musculus

<400> SEQUENCE: 9
aagtgactca gtg                                                 13

<210> SEQ ID NO 10
<211> LENGTH: 13
<212> TYPE: DNA
<213> ORGANISM: Rat

<400> SEQUENCE: 10
aagtgactca gtg                                                 13

<210> SEQ ID NO 11
<211> LENGTH: 13
<212> TYPE: DNA
<213> ORGANISM: Homo sapiens

<400> SEQUENCE: 11
aagtgactca gcg                                                 13

<210> SEQ ID NO 12
<211> LENGTH: 13
<212> TYPE: DNA
<213> ORGANISM: Orangutan
```

-continued

```
<400> SEQUENCE: 12
aagtgactca gcg                                                          13

<210> SEQ ID NO 13
<211> LENGTH: 13
<212> TYPE: DNA
<213> ORGANISM: dog

<400> SEQUENCE: 13
aagtgactca gcg                                                          13

<210> SEQ ID NO 14
<211> LENGTH: 13
<212> TYPE: DNA
<213> ORGANISM: horse

<400> SEQUENCE: 14
aagtgactca gcg                                                          13

<210> SEQ ID NO 15
<211> LENGTH: 13
<212> TYPE: DNA
<213> ORGANISM: opossum

<400> SEQUENCE: 15
aaatgactca gcg                                                          13

<210> SEQ ID NO 16
<211> LENGTH: 13
<212> TYPE: DNA
<213> ORGANISM: chicken

<400> SEQUENCE: 16
aaatgagtca gcg                                                          13

<210> SEQ ID NO 17
<211> LENGTH: 22
<212> TYPE: DNA
<213> ORGANISM: Homo sapiens

<400> SEQUENCE: 17
cgcttgattg actcagccgg aa                                                22

<210> SEQ ID NO 18
<211> LENGTH: 21
<212> TYPE: DNA
<213> ORGANISM: Homo sapiens

<400> SEQUENCE: 18
ttccggctga ctcatcaagc g                                                 21

<210> SEQ ID NO 19
<211> LENGTH: 21
<212> TYPE: DNA
<213> ORGANISM: Homo sapiens

<400> SEQUENCE: 19
cgcttgatga ctcagccgga a                                                 21

<210> SEQ ID NO 20
<211> LENGTH: 21
<212> TYPE: DNA
```

```
<213> ORGANISM: Homo sapiens

<400> SEQUENCE: 20
ttccggccaa gtcatcaagc g                                            21

<210> SEQ ID NO 21
<211> LENGTH: 19
<212> TYPE: DNA
<213> ORGANISM: Homo sapiens

<400> SEQUENCE: 21
taaaagtgac tcagtggct                                               19

<210> SEQ ID NO 22
<211> LENGTH: 19
<212> TYPE: DNA
<213> ORGANISM: Homo sapiens

<400> SEQUENCE: 22
agccactgac tcactttta                                               19

<210> SEQ ID NO 23
<211> LENGTH: 19
<212> TYPE: DNA
<213> ORGANISM: Homo sapiens

<400> SEQUENCE: 23
taaaagtgac ttggtggct                                               19

<210> SEQ ID NO 24
<211> LENGTH: 19
<212> TYPE: DNA
<213> ORGANISM: Homo sapiens

<400> SEQUENCE: 24
agccaccaag tcactttta                                               19
```

METHODS INVOLVING PDGFRBETA INHIBITORS

This application is a national phase application under 35 U.S.C. §371 of International Application No. PCT/EP2010/064367 filed 28 Sep. 2010, which claims priority to European Application No. 09171469.1 filed 28 Sep. 2009, and U.S. Provisional Application No. 61/262,526 filed 11 Nov. 2009. The entire contents of each of the above-referenced applications is specifically incorporated herein by reference without disclaimer.

The invention refers to a new indication for PDGFRbeta inhibitors. Platelet-derived growth factor receptor beta polypeptide, also known as PDGFRB, PDGFRbeta, PDGF-Rβ or CD140B, is a human gene, encoding a cell surface tyrosine kinase receptor for members of the platelet-derived growth factor family. These growth factors are mitogens for cells of mesenchymal origin. The identity of the growth factor bound to a receptor monomer determines whether the functional receptor is a homodimer or a heterodimer, composed of both platelet-derived growth factor receptor alpha and beta polypeptides. This gene is flanked on chromosome 5 by the genes for granulocyte-macrophage colony-stimulating factor and macrophage-colony stimulating factor receptor; all three genes may be implicated in the 5-q syndrome. A translocation between chromosomes 5 and 12, that fuses this gene to that of the translocation, ETV6, leukemia gene, results in chronic myeloproliferative disorder with eosinophilia.

WO 2005/075454 A2 discloses the use of imatinib for the treatment of various cancer diseases, including leukemia. WO 2008/037716 A2 discloses the use of nilotinib for the treatment of chronic myelod leukemia and gastrointestinal stromal tumors. Verbeek et al. (Nat. Rev. Clin. One. 7 (2010) 116-119) disclose an imatinib-induced T-cell proliferative disorder in a patient with gastrointestinal stromal tumor. Rassidakis et al. (Mod. Pathol 17 (2004) 946-953; and Blood 102 (2003), 4619-4620) report that c-kit is not expressed in Hodgkin's Disease and anaplastic lymphoma kinase- (ALK-) positive anaplastic large-cell lymphomas (ALCL) cell lines, thereby making c-kit not an appropriate target for therapeutic agents such as imatinib. Pullarkat et al. (Leuk. Res. 32 (2008), 1770-1775) describe a patient with a megakaryocytic blast crisis as the presenting manifestation of chronic myeloid crisis wherein treatment with imatinib was ineffective.

WO 2007/053573 A2 discloses compositions and methods for treating a long list of several hundreds of tumor diseases, i.a. ALCL with effective amounts of sorafenib.

Lansigan et al. (J. Clin. Oncol. 28 (2010) TPS 300 disclose a pilot study of sorafenib in relapsed or refractory T-cell lymphomas. On the other side, Ambrosini et al. describe that sorafenib is not effective in in vivo treatment of HD and ALCL, although it was able to induce apoptosis in human ACLC/HD-cell lines (also: Nguyen et al., Leuk. Res. 34 (2010), 379-386).

US 2005/0119352 A discloses that e.g. HD can be treated by administration of a cell cycle checkpoint activator, which is preferably beta-lapachone, or a derivative or analog thereof, combined with an oncogenic kinase modulator, preferably imatinib.

In view of the prior art, reports on potential treatments of lymphoma of T-cell origin were completely contradictory. Accordingly, the need for a reliable and effective treatment for such patients, especially ALCL patients is still unment, but remains essential.

Therefore, the present invention provides a PDGFRB inhibitor for the antiproliferative treatment of T-cell lymphoma in patients susceptible to a cell proliferative disorder. Thereby tumor proliferation may be effectively prevented. The inhibitor according to the invention can be used for the treatment of all lymphomas. Preferably, the lymphoma is selected from the group consisting of NHL, ALCL and PTCL.

The inhibitor according to the invention is particularly useful for treating relapsed patients. Thus, a particularly preferred treatment is the second-line treatment of drug-resistant patients.

In an alternative embodiment the inhibitor according to the invention is used for first line therapy of patients.

The inhibitor according to the invention preferably is selected from PDGFRB antagonists, such as polypeptides or small molecules.

In a specific embodiment the inhibitor according to the invention is selected from the group consisting of nilotinib, imatinib, dasatinib, sorafenib, axitinib, sunitinib and toceranib.

The therapeutic method employing the inhibitor according to the invention preferably is for prophylactic or therapeutic use.

Preferably the inhibitor according to the invention is formulated for local or systemic use, more preferably for oral use.

A preferred treatment regiment provides for an inhibitor, like imatinib, at a dose ranging from 0.001 mg/kg/day to about 100 mg/kg/day. Thus, the preferred inhibitor according to the invention is formulated to provide for administration of such a dose.

A preferred embodiment of the invention relates to the use of the inhibitor in combination with chemotherapy and/or radiation therapy, including CHOP therapy or modifications of this therapy (8).

The invention further provides for a method of preparing a pharmaceutical preparation containing a PDGFRbeta inhibitor for the treatment of T-cell lymphoma. PDGFs (platelet derived growth factors) are essential for blood vessel formation, growth stimulation of tumor cells, tumor angiogenesis and recruitment and regulation of tumor fibroblasts. There are four different ligands (PDGF A-D) which can form homo- or heterodimers and bind to two different receptors (PDGFRA and PDGFRB).

Activated tyrosine kinases are implicated in the pathogenesis of chronic and acute leukemia, and represent attractive targets for inhibitor therapy. Several inhibitors are used in cancer therapy.

Imatinib (4-[(4-methylpiperazin-1-yl)methyl]-N-[4-methyl-3-[(4-pyridin-3-ylpyrimidin-2-yl)amino]phenyl]benzamide) is a drug used to treat certain types of cancer. It is currently marketed by Novartis as Gleevec® (USA) or Glivec® (Europe/Australia) as its mesylate salt, imatinib mesilate (INN). It is used in treating chronic myelogenous leukemia (CML), gastrointestinal stromal tumors (GISTs) and a number of other malignancies. Imatinib may also have a role in the treatment of pulmonary hypertension. It has been shown to reduce both the smooth muscle hypertrophy and hyperplasia of the pulmonary vasculature in a variety of disease processes, including portopulmonary hypertension.

Imatinib functions as a specific inhibitor of a number of tyrosine kinase (TK) enzymes. It occupies the TK active site, leading to a decrease in activity. There are a large number of TK enzymes in the body, including the insulin receptor. Imatinib is specific for the TK domain in abl (the Abelson protooncogene), c-kit and PDGF-R (platelet-derived growth factor receptor).

In laboratory settings, imatinib is being used as an experimental agent to suppress platelet-derived growth factor by inhibiting its receptor PDGFRB. One of its effects is delaying atherosclerosis in mice with diabetes.

In chronic myelogenous leukemia, the Philadelphia chromosome leads to a fusion protein of abl with bcr (breakpoint cluster region), termed bcr-abl. As this is now a continuously active tyrosine kinase, imatinib is used to decrease bcr-abl activity.

The active sites of tyrosine kinases each have a binding site for ATP. The enzymatic activity catalyzed by a tyrosine kinase is the transfer of the terminal phosphate from ATP to tyrosine residues on its substrates, a process known as protein tyrosine phosphorylation. Imatinib works by binding to the ATP binding site of bcr-abl and inhibiting the enzyme activity of the protein competitively.

Imatinib is quite selective for bcr-abl—it does also inhibit other targets mentioned above (c-kit and PDGF-R), but no other known tyrosine kinases.

Nilotinib (4-methyl-N-[3-(4-methyl-1H-imidazol-1-yl)-5-(trifluoromethyl)phenyl]-3-[(4-pyridin-3-ylpyrimidin-2-yl)amino]benzamide), in the form of the hydrochloride monohydrate salt, is a tyrosine kinase inhibitor, which inhibits bcr-abl as well.

It was approved as Tasigna® in the USA and the EU for second line treatment drug-resistant, Philadelphia chromosome positive chronic myelogenous leukemia (CML). Nilotinib shows activity in cases of CML resistant to treatment with imatinib, which is currently used as a first-line treatment.

Another bcr-abl inhibitor used as anti-neoplastic agent is dasatinib (N-(2-chloro-6-methylphenyl)-2-[[6-[4-(2-hydroxyethyl)-1-piperazinyl]-2-methyl-4-pyrimidinyl]amino]-5-thiazole carboxamide monohydrate, distributed by Bristol-Myers Squibb under the brand name SPRYCEL®), which has shown activity in chronic-phase CML.

Sorafenib (4-[4-[[4-chloro-3-(trifluoromethyl)phenyl]carbamoylamino]phenoxy]-N-methyl-pyridine-2-carboxamide, Nexavar®, Bayer) is a small molecule B-RAF inhibitor that is used for the treatment of renal cell carcinoma, and has been shown to have activity against receptor tyrosine kinases from the platelet-derived growth factor receptor (PDGFR) and vascular endothelial growth factor receptor (VEGFR) families. In WO 2007/053573 A2 sorafenib was suggested to be used in a long list of several hundreds of tumor diseases, i.a. ALCL. However, this document is non enabling for a person skilled in the art and only of speculative nature. Accordingly, sorafenib is not regarded as a preferred PDGFRbeta inhibitor according to the present invention but can be regarded as being disclaimed from this group of compounds, at least as far as the treatment of ALCL in general is concerned.

Axitinib (N-Methyl-2-[[3-[(E)-2-pyridin-2-ylethenyl]-1H-indazol-6-yl]sulfanyl]benzamide, also known as AG013736) is a small molecule tyrosine kinase inhibitor under development by Pfizer. It inhibits multiple targets, including VEGFR-1, VEGFR-2, VEGFR-3, platelet derived growth factor receptor (PDGFR), and c-Kit (CD117). It has been shown to significantly inhibit growth of breast cancer in xenograft models and has been successful in trials with renal cell carcinoma (RCC) and several other tumor types.

Sunitinib (N-[2-(diethylamino)ethyl]-5-[(Z)-(5-fluoro-1,2-dihydro-2-oxo-3H-indol-3-ylidine)methyl]-2,4-dimethyl-1H-pyrrole-3-carboxamide, Sutent®, Pfizer) inhibits cellular signaling by targeting multiple receptor tyrosine kinases (RTKs), including those receptors for platelet-derived growth factor and vascular endothelial growth factor receptors (VEGFRs), which play a role in both tumor angiogenesis and tumor cell proliferation. The simultaneous inhibition of these targets therefore leads to both reduced tumor vascularization and cancer cell death, and ultimately tumor shrinkage. It has been recommended as a second-line therapy for patients whose tumors develop mutations in c-kit that make them resistant to imatinib, or who become intolerant to the drug.

Toceranib ((Z)-5-[(5-Fluoro-2-oxo-1,2-dihydro-3H-indol-3-ylidene)methyl]-2,4-dimethyl-N-(2-pyrrolidin-1-yl-ethyl)-1H-pyrrole-3-carboxamide) is a receptor tyrosine kinase inhibitor and is used in the treatment of canine mast cell tumor also called Mastocytoma. It is the only dog-specific anti-cancer drug approved by the U.S. Food and Drug Administration. It is marketed as Palladia® as its phosphate salt, toceranib phosphate (INN) by Pfizer. Toceranib belongs to the class of tyrosine kinase inhibitors. Toceranib is designed to target a specific tumor cell receptor called c-Kit, which is mutated in 25-50% of canine mast cell tumors, and two other blood vessel cell receptors involved in tumor angiogenesis, PDGFR and VEGFR.

Anaplastic Large Cell Lymphoma (ALCL) is a highly malignant form of Non-Hodgkin's lymphoma, mainly of T-cell origin. It comprises about 5% of all Non-Hodgkin's lymphoma cases. About 50% of ALCL patients carry the translocation t(2;5)(p23;q35), which generates the oncogenic fusion protein NPM-ALK (nucleophosmin-anaplastic lymphoma kinase). Fusions with other proteins such as ATIC, CLTCL, MSN, RanBP2, TFG and TPM3 have been observed, although with a much lower frequency.

ALK is a transmembrane receptor tyrosine kinase (RTK) of the insulin receptor superfamily. Endogenous ALK expression is restricted to the nervous system. It is most abundant in the neonatal brain, and is sustained in the adult brain, albeit at a lower level. Regarding the exact function of ALK, research is ongoing, although strong evidence has been presented for ALK being a pleiotropin receptor. Contrary to oncogenic ALK-fusion proteins, endogenous ALK is not expressed in haematopoietic tissues.

NPM (Nucleophosmin) is a nucleolar protein that is involved in ribosome biogenesis and centrosome duplication, is upregulated in response to stress stimuli and modulates the function of several tumor suppressor genes.

Constitutive overexpression and activation of NPM-ALK fusion protein [t(2:5)(p23;q35)] is a key oncogenic event that drives the survival and proliferation of ALCLs.

The catalytic part of the receptor tyrosine kinase ALK fuses with the oligomerization domain of the RNA-binding nucleolar phosphoprotein NPM. This leads to the constitutive activation of ALK through homodimerization and autophosphorylation of NPM-ALK and expression of ALK in lymphoid ALCL cells. The aberrant expression of ALK is directly involved in the formation of ALCL.

Galkin et al. (PNAS 104 (2007), 270-275) have identified a highly potent and selective small molecule ALK inhibitor, NVP-TAE684, which blocked the growth of ALCL-derived and ALK-dependent cell lines with IC50 values between 2 and 10 nM. NVP-TAE684 was shown to suppress lymphomagenesis in two independent models of ALK-positive ALCL and induced regression of established Karpas-299 lymphomas in vivo. NVP-TAE684 also induced down-regulation of CD30 expression, suggesting that CD30 may be used as a biomarker of therapeutic NPM-ALK kinase activity inhibition.

NPM-ALK has transforming activities in vitro and in vivo and is interacting with a wide range of oncogenic factors and signaling networks, such as Jak/Stat or PI3K/Akt. ALK positive (ALK$^+$) ALCLs are as well characterized by high expression of the cytokine receptor CD30 and the activator protein (AP-1) transcription factor family members JunB and cJun.

AP-1 is a DNA-binding transcription factor and important player in many processes, including cell proliferation, differentiation and apoptosis, as well as oncogenic transformation. It consists of the Jun family members (cJun, JunB, JunD) which form homodimers or heterodimers with Fos or ATF family members. JunB and cJun often have antagonistic functions. JunB has been reported to be either proapoptotic or antiapoptotic, depending on the cellular context. In ALCL, JunB and cJun have been found to be overexpressed and a role for JunB in activating CD30 has been described. Thus, cJun and JunB are implicated in tumor proliferation (Mathas et al., EMBO J. 21 (2002), 4104-4113; Kenner et al., J. Cell Biol. 164 (2004), 613-623; Watanabe et al., Can. Res. 65 (2005), 7628-7634; Jacobsen, The Oncologist 11 (2006), 831-840).

Systemic ALCL is a progressive disease that can ultimately prove fatal.

Patients diagnosed with systemic ALCL are often treated with CHOP as a first approach to therapy. CHOP is a combination of several chemotherapy drugs (Cyclophosphamide, Hydroxydaunomycin (doxorubicin), Oncovin® (vincristine), and Prednisone). Other combinations of chemotherapy may also be used as a first option.

In addition, radiation therapy can be an important adjunct to therapy when there are particularly large masses of lymphoma in a localized area or when local large lymph nodes are compressing or invading normal organs or structures and chemotherapy cannot control the problem.

Treatment options following first-line combination therapy may include alternative higher dose chemotherapy regimens combined with radiation therapy. High dose combination therapy such as this targets the lymphoma cells in the tumor as well as lymphoma cells which may be located in the bone marrow. However, normal blood forming cells in the bone marrow may also be killed. Because of this, bone marrow transplantation or transplantation of circulating blood stem cells collected from the patient's own blood or that of a tissue-matched relative or unrelated donor is required. Patients who are resistant to or who relapse following such treatments have limited therapeutic options

ANALYTICAL METHODS

Real Time PCR

Figure 1A:
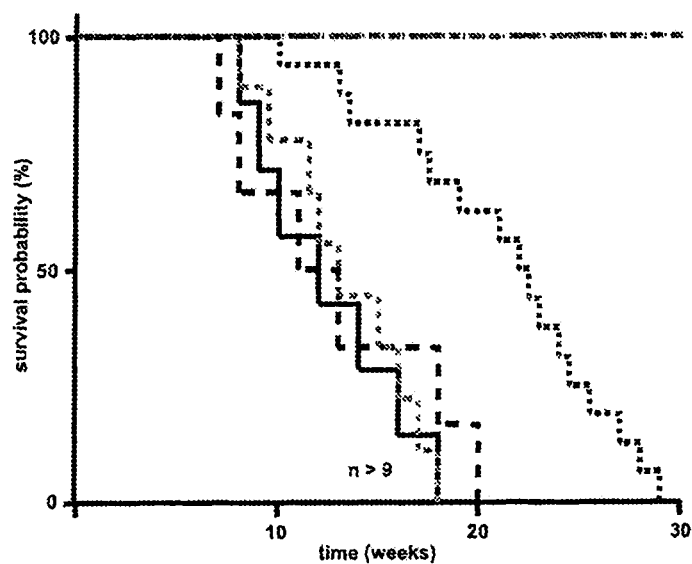
FIG. 1: T cell specific knockout of JunB together with cJun significantly increases the survival time of NPM-ALK transgenic mice (G. Inghirami; University of Turin). (a) We used five groups of mice, NPM-ALK, NPM-ALK$^{\Delta JunB}$ (E.F. Wagner), NPM-ALK$^{\Delta cJun}$ (E.F. Wagner), NPM-ALK$^{\Delta Jun}$ and wild type mice. While NPM-ALK$^{\Delta Jun}$ mice lived significantly longer than NPM-ALK mice, there was no difference in the survival times of NPM-ALK$^{\Delta JunB}$ and NPM-ALK$^{\Delta cJun}$ mice. (b) Analysis of NPM-ALK, JunB and cJun mRNA levels by qRT-PCR. NPM-ALK mRNA expression level is similar in NPM-ALK and NPM-ALK$^{\Delta Jun}$ tumors, but absent in wild type thymus. JunB expression is high in wild type thymus and NPM-ALK tumors and absent in NPM-ALK$^{\Delta Jun}$ tumors. CJun expression is high in NPM-ALK lymphomas and wild type spleen, but absent in NPM-ALK$^{\Delta Jun}$ tumors. (c) Analysis of NPM-ALK, JunB and cJun protein levels by Western Blot. ALK levels are equal in NPM-ALK and NPM-ALK$^{\Delta Jun}$ tumors, while JunB and cJun are present in NPM-ALK, but absent in NPM-ALK$^{\Delta Jun}$ tumors.

Real Time PCR was performed with SybrGreen PCR qPCR Supermix for ABI Prism (Invitrogen), according to the manufacturer's standard protocol on a Chromo 4 cycler (Biorad). 50 ng of cDNA was used per well, every sample was analyzed in triplicates, GAPDH was used for normalization. Results were analyzed with the 2-ΔΔCt metho. Primers: NPM-ALK FW: GTG GTC TTA AGG TTG AAG TGT GGT T (SEQ ID NO: 1); NPM-ALK Rev: GCT TCC GGC GGT ACA CTA CTA A (SEQ ID NO: 2); JunB FW: GGC TTT GCG GAO GGT TT (SEQ ID NO: 3); JunB Rev: GGC GTC ACG TGG TTC ATC T (SEQ ID NO: 4); c-jun FW: TGA CTG CAA AGA TGG AAA CG (SEQ ID NO: 5); c-jun Rev: GCT CTC GGA CTG GAG GAA C (SEQ ID NO: 6); PDG-FRB FW: TGC CAG TTC CAC CTT GAA TGA A (SEQ ID NO: 7); PDGFRB Rev: AGT TGT GCC TCA GGC TCT GCT T (SEQ ID NO: 8).

Western Blot

Approximately 100 mg of tumor tissue was cut up in 1 ml of lysis buffer consisting of 50 mM Tris-HCl pH 7.4, 150 mM NaCl, 0.1% Triton X-100, 5 mM EDTA, 1× complete proteinase inhibitor (Roche), 1×HALT phosphatase inhibitor (Thermo scientific) with a Dounce on Ice. The resulting suspension was then centrifuged for 5 min at 1200 rpm, the supernatant was transferred to a new tube and the protein concentration was measured with a Qubit fluorometer (Invitrogen). Total protein lysates (50 μg) were subjected to sodium dodecyl sulphate-polyacrylamide electrophoresis (SDS-PAGE) and then transferred to a nitrocellulose membrane.

The membrane was blocked in TBS-T plus 1% milk+1% Polyvinylpyrolidone (PVP) for 1 h before incubating over night at 4° C. with the primary antibody (diluted to the proper concentration in TBS-T plus 1% milk+1% PVP (Polyvinylpyrolidone and 0.02% NaN$_3$). Thereafter, the membrane was washed three times with TBS-T and incubated for 1 h with the appropriate secondary antibody, diluted in TBS-T. After a final washing step with TBS, the membrane was incubated for 1 min with the ECL Plus solution (Amersham Biosciences) and then the picture taken on a Luminometer (Roche). Following primary antibodies were used: anti-JunB sc-73X, anti-c-jun sc-1694X (Santa Cruz), anti-PDGFRB #3169 (Cell Signalling), anti-Betaactin #4967 (Cell Signalling), anti-Alk 51-3900 Zymed; anti-phospho-Alk (#33415, Cell Signalling), Santa Cruz), anti-cKit (sc-168, Santa Cruz).

Immunohistochemistry and Immunofluorescence

Formalin fixed paraffin embedded (FFPE) tumor samples were cut, attached to slides, dewaxed and rehydrated. Epitopes were retrieved by heat treatment in Tris-EDTA. Endogenous peroxidase was blocked in 3% H$_2$O$_2$ for 10 min. Sections were blocked in Avidin/Biotin block (Vector), Superblock and mouse block from the Universal Mouse HRP-Kit (IDLabs). Primary antibody staining was done at 4° C. over night. AEC and heamatoxylin was used as counterstain. Antibodies used were anti-PDGFRB (Cell Signalling, #3169), anti-JunB (Santa Cruz, sc-46), anti-c-jun (Santa Cruz, sc-1694), anti-Alk Zymed (51-3900) were used according to the manufacturers instructions. Haematoxilin/Eosin and PAS staining were performed with staining kits from DAKO.

The present inventors have now discovered a therapeutic strategy that addresses treatment of T-cell lymphoma by inhibition of PDGFRB activation. Such inhibition is relevant for modulation of cell proliferation and apoptosis, particularly in certain AP-1 positive cancer types. The present invention relates, at least in part, to the discovery that the PDGFRB activation mediated processes are useful as targets (e.g., selective) for T-cell lymphoma tumor therapy, in particular for treating aggressive NHL or ALCL.

There is evidence in the prior art for the relationship between ALCL and NPM-ALK. However, the activation of PDGFRB in NPM-ALK positive ALCL was surprising. Although PDGFRB could be found to be overexpressed in NPM-ALK induced lymphoma, several studies demonstrated that the use of a PDGFRB inhibitor, such as imatinib, would not have a beneficial effect on ALCL cell lines (Rassidakis et al., Blood 105 (2005), 827-829; Ergin et al., Exp. Hematol. 29 (2001): 1082-1090). NPM-ALK was also found to be insensitive to imatinib treatment (Gunby et al., J. Med. Chem. 49 (2006), 5759-5768).

The unique effect of a PDGFRB activator inhibitor in an animal model of AP-1 expressing lymphoma was thus surprising.

The term "administration" includes routes of introducing the inhibitor of the invention to a subject in need thereof to perform their intended function. Examples of routes of administration that may be used include oral administration. The inhibitor can also be administered by any other convenient route, for example, by continuous infusion or bolus injection, by absorption through epithelial or mucocutaneous linings (e.g., oral, rectal, vaginal, and intestinal mucosa, etc.) and can be administered together with another therapeutic agent. Administration can be systemic or local. Various known delivery systems, including encapsulation in liposomes, microparticles, microcapsules, and capsules, can be used. Methods of administration of the inhibitor of this invention include, but are not limited to, intradermal, intramuscular, intraperitoneal, intravenous, subcutaneous, intranasal, epidural, oral, sublingual, intracerebral, intravaginal, transdermal, rectal, by inhalation, or topical. The inhibitor of the invention can be administered alone, or in conjunction with either another PDGFRB inhibitory agent or any other therapeutic agent used in the treating T-cell lymphoma, or both, preferably together with a pharmaceutically-acceptable carrier. The inhibitor of the invention can be administered prior to the administration of the other agent, simultaneously with the agent, or after the administration of the agent. Furthermore, the inhibitor of the invention can also be administered in a pro-drug form which is converted into its active metabolite, or more active metabolite in vivo.

The term "PDGFRB inhibitor" refers to a ligand that binds to PDGFRB (e.g., full length, N-terminus, C-terminus, carboxy terminus, ATP binding pocket of the kinase domain) thereby preventing its activation, and/or directly or indirectly exhibits functional inhibition of PDGFRB activation. The inhibiting activity may be tested by the following standard test, like HTScan® PDGF Receptor β Kinase Assay Kit #7770; Cell signalling.

The term "a prophylactically effective amount" refers to an amount of an inhibitor of the invention, which is effective, upon single or multiple dose administration to the patient, in preventing or treating a cell proliferative disorder.

The term "subject" includes organisms which are capable of suffering from a cell proliferative disorder or who could otherwise benefit from the administration of a compound of the invention, such as human and non-human animals. Preferred humans include human patients suffering from or prone to suffering from a cell proliferative disorder or associated state, as described herein. The term "non-human animals" of the invention includes all vertebrates, e.g., mammals, rodents, such as mice, and non-mammals, such as non-human primates, e.g., sheep, dog, cow, chickens, which are preferably used as animal models of human T-cell lymphoma.

The term "susceptible to a cell proliferative disorder" is meant to include
subjects at risk of developing disorder of cell proliferation, e.g., cancer, i.e., subjects suffering from viral infection with cancer viruses, subjects that have been exposed to ionizing radiation or carcinogenic compounds, subjects having a family or medical history of cancer, and the like.

The term "therapy" or "treatment" as used herein includes both, prophylactic or therapeutic measures to treat patients susceptible to a cell proliferative disorder.

In a specific embodiment, the invention provides methods for treating a subject for a T-cell proliferative disorder, by administering to the subject an effective amount of a PDGFRB inhibitor capable of inhibiting proliferation of T-cell lymphoma cells. A T-cell proliferative disorder includes cancer, in particular late stage cancer.

The inhibitor according to the invention is preferably used in NPM-ALK lymphomas, such as non-Hodgkin lymphoma, or NHL, in particular aggressive NHL, e.g. for use in ALCL, such as systemic ALCL, involving lymph nodes or extranodal sites, or primary cutaneous ALCL, involving skin nodules. Likewise the inhibitor according to the invention may be indicated for use in other aggressive mature T-/NK-cell lymphomas, for instance to treat peripheral T-cell lymphoma (PTCL), e.g. in lymphoid tissues of post-thymic origin, such as lymph nodes. In particular those T-cell lymphoma patients are treated with an inhibitor according to the invention, where the overexpression of PDGFRB has proven. Overexpression is preferably determined by the increased expression in biological samples, which increase is at least 1.2 times, more preferably at least 1.5 times the reference value of subjects not susceptible to or suffering from the T-cell lymphoma.

The most preferred embodiment according to the present invention is the treatment of ALK+ T-cell lymphomas, especially ALK$^+$-ALCL, i.e. ALCL wherein the tumor cells are ALK positive (especially NPM-ALK$^+$). In view of the prior art wherein it was confirmed that in these tumours the target of substances like imatinib, c-kit, was missing, it was highly surprising that the treatment with PDGFRbeta inhibitors according to the present invention, preferably with nilotinib, imatinib, dasatinib, axitinib, sunitinib or toceranib, especially with imatinib or nilotinib, was effective. In the course of this specific treatment it is therefore preferred to check the ALK status of an ALCL patient first and then decide about the most effective treatment. This can be done by methods known in the prior art, e.g. by providing a sample of tumor cells from the patient (e.g. a blood, serum or plasma sample of the patient and then to check whether these cells are ALK$^+$ or ALK$^-$ (e.g. Ergin et al., 2001; Formari et al., Hematol. Oncol. 27 (2009), 161-170). Although imatinib is unable to bind ALK and is unable to show effects in human ALK positive ALCL cell lines (see Ergin et al., 2001), ALK positive (especially NPM-ALK positive) ALCL can successfully be treated in human ALCL patients with PDGFRbeta inhibitors, preferably with nilotinib, imatinib, dasatinib, axitinib, sunitinib or toceranib, especially with imatinib or nilotinib. Also for this preferred embodiment, presence of (expression of) AP-1 is necessary.

Accordingly, in a preferred method for treatment of antiproliferative treatment ALK expressing lymphomas, preferably ALK$^+$-ALCL, especially in NPM-ALK$^+$-ALCL, according to the present invention, first a sample of a patient having a lymphoma and containing tumor cells is analysed whether said tumor cells express ALK; and, if the tumor cells of said sample express ALK, said patient is treated with an effective amount of a PDGFRbeta inhibitor, preferably with a PDGFRbeta inhibitor selected from nilotinib, imatinib, dasatinib, axitinib, sunitinib or toceranib, especally with imatinib or nilotinib.

In certain embodiments, the subject is a mammal, e.g. a primate, including a human or a non-human primate. In this embodiment, the inhibitor of the invention may either directly or indirectly interact with PDGFRB, or specific domains thereof. A cell undergoing uncontrolled proliferation can be contacted with an inhibitor of the invention to inhibit cell proliferation or induce apoptosis. Contacting cells or administering the inhibitor of the invention to a subject is one method of treating a cell or a subject suffering from or susceptible to a cell proliferative disorder.

According to a certain embodiment, a method of treating a subject suffering from or susceptible to a T-cell lymphoma disorder includes administering to a subject in need thereof a prophylactically or therapeutically effective amount of an inhibitor of PDGFRB, such that it inhibits AP-1 expressing lymphoma cells. Exemplary inhibitors include those TK inhibitors having at least partial specificity to bind PDGFRB, pharmaceutically acceptable salts thereof or analogues identified through standard screening methods.

According to the invention preferred small molecule inhibitors are those commercially available compounds that have been used in anti-cancer therapy for a different purpose, like nilotinib, imatinib, dasatinib, sorafenib, axitinib, sunitinib and toceranib or functional derivatives thereof with proven inhibiting activity.

Further inhibitors of PDGFR could be identified by appropriate screening technology employing the test for the inhibiting activity.

Also preferred are polypeptide inhibitors, which mimic the structure of the natural PDGF binding partner, or which are specific immunoligands to PDGFRB compounds, such as antagonistic monoclonal antibodies or antibody fragments.

Those inhibitory agents are preferred that bind to PDGFRB with a high affinity, preferably with a Kd of less than $10^{-6}$ M.

In certain embodiments, the methods of the invention include administering to a subject a therapeutically effective amount of an inhibitor of the invention in combination with another pharmaceutically active agent or conventional treatment methods. Examples of pharmaceutically active compounds include other PDGFRB inhibitors and/or agents known to treat T-cell proliferative disorders, e.g. an anticancer agent, an antiproliferative agent or a chemotherapeutic. Conventional treatment regimens for T-cell lymphoma, which are easily combined with the inhibitors of the invention, are standard chemotherapy and/radiation therpy, including the use of a short pulse chemotherapy or CHOP therapy (Seidemann et al., Blood 97 (2001), 3699-3706). The present invention, further relates to kits comprising the inhibitor of the invention and drugs as used for combination therapy.

The inhibitor of the invention and the pharmaceutically active compound may be administered to the subject in the same pharmaceutical composition or in different pharmaceutical compositions, e.g. at the same time or at different times.

Determination of a therapeutically effective amount or a prophylactically effective amount of the inhibitor according to the invention can be readily made by one skilled in the art, by the use of known techniques and by observing results obtained under analogous circumstances. In vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a skilled artisan.

The effective amount of an inhibitor of the invention, either therapeutically or prophylactically used, is expected to vary from about 0.001 milligram per kilogram of body weight per day (mg/kg/day) to about 100 mg/kg/day. A preferred dose range is from 0.1 to 10 mg/kg/day. Further preferred doses range from 0.01 to 10 g/day, more preferably 0.1 to 1 g/day, more preferred 0.1-0.5 g/day, in particular 200-400 mg/day.

In a further another aspect of the invention, a method is provided to identify an inhibitor suitable for PDGFRB inhibition in treating T-cell lymphoma. Functional assays involve the ex vivo use of T-cell lymphoma cell lines derived from subjects suffering from such disorder, which have proven PDGFRB overexpression.

Methods to determine PDGFRB inhibiting activity in vitro include obtaining the crystal structure of PDGFRB, or specific domains thereof in the presence and/or absence of a test compound. Compounds may then be computer modeled into or on the binding site of the crystal structure. Once potential modulating compounds are identified, the compounds may be screened using in vitro, in vivo, or ex vivo cellular assays. Compounds identified in this manner are useful as analogues of the preferred inhibitors of the invention.

The inhibitor of the invention may be formulated in an effective amount with a pharmaceutically acceptable carrier or diluent. For example, an effective amount is provided in a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject, including tablets, lozenges, buccal forms, troches, aqueous or oily suspensions or solutions, granules, powders, pastes, emulsions, capsules, syrups or elixirs.

Exemplary formulations as used for parenteral administration include subcutaneous, intramuscular or intravenous injection as, for example, a sterile solution or suspension. Formulations for topical application include a number of forms such as creams or ointments, pastes and gels.

Preferred pharmaceutically-acceptable carrier include vehicles, like sugars, such as lactose, glucose and sucrose, starches, such as corn starch and potato starch, cellulose and its derivatives, such as sodium carboxymethyl cellulose, ethyl cellulose and cellulose acetate, or polyols, such as glycerin, sorbitol, mannitol and polyethylene glycol, or other diluents and excipients known in the art to be employed in pharmaceutical formulations. Suitable examples of liquid carriers for oral and parenteral administration include water, particular containing additives as above, e.g. cellulose derivatives, including sodium carboxymethyl cellulose solution, alcohols including monohydric alcohols and polyhydric alcohols and their derivatives, and oils. The physiologically acceptable excipients can be saline, gelatin, starch, talc, keratin, colloidal silica, urea and the like. In addition, auxiliary, stabilizing, thickening, lubricating, and coloring agents can be used.

They may also be formulated so as to provide sustained or controlled release of the active ingredient therein using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. The inhibitor can also be in micro-encapsulated form, with one or more of the above-described excipients.

The subject matter of the following definitions are embodiments of the present invention:

1. PDGFRbeta inhibitor for the antiproliferative treatment of T-cell lymphoma in patients susceptible to a cell proliferative disorder.

2. Inhibitor according to claim 1, for the treatment of AP-1 expressing lymphoma.

3. Inhibitor according to claim 1 or 2, for the treatment of lymphoma selected from the group consisting of NHL, ALCL, preferably ALK$^+$-ALCL, especially in NPM-ALK$^+$-ALCL, and PTCL.

4. Inhibitor according to any of claims 1 to 3, for treating relapsed patients.

5. Inhibitor according to any of claims 1 to 4, for first line therapy of patients.

6. Inhibitor according to any of claims 1 to 5, which is selected from PDGFRbeta antagonists, such as polypeptides or small molecules.
7. Inhibitor according to claim 6, which is selected from the group consisting of nilotinib, imatinib, dasatinib, axitinib, sunitinib and toceranib, especially imatinib or nilotinib.
8. Inhibitor according to any of claims 1 to 7, for prophylactic or therapeutic use.
9. Inhibitor according to any of claims 1 to 8, which is formulated for local or systemic use.
10. Inhibitor according to any of claims 1 to 9, which is formulated for oral use.
11. Inhibitor according to any of claims 1 to 10, which is administered at a dose ranging from 0.001 mg/kg/day to about 100 mg/kg/day.
12. Inhibitor according to any of claims 1 to 11, for use in combination with chemotherapy and/or radiation therapy.
13. PDGFRbeta inhibitor, selected from nilotinib, imatinib, dasatinib, axitinib, sunitinib or toceranib, especially imatinib or nilotinib, for use in the antiproliferative treatment of T-cell lymphoma, specifically AP-1 expressing ALCL, preferably ALK$^+$-ALCL, especially in NPM-ALK$^+$-ALCL.
14. Method of preparing a pharmaceutical preparation containing a PDGFRbeta inhibitor for the antiproliferative treatment of T-cell lymphoma.
15. A method for antiproliferative treatment of T-cell lymphoma, specifically AP-1 expressing and ALK expressing lymphomas, preferably ALK$^+$-ALCL, especially in NPM-ALK$^+$-ALCL, wherein a sample of a patient having a lymphoma and containing tumor cells is analysed whether said tumor cells express AP-1 and/or ALK; and, if the tumor cells of said sample express AP-1 and ALK, treat said patient with an effective amount of a PDGFRbeta inhibitor, preferably with a PDGFRbeta inhibitor selected from nilotinib, imatinib, dasatinib, axitinib, sunitinib or toceranib, especially with imatinib or nilotinib.
16. PDGFRbeta inhibitor for use in the antiproliferative treatment of AP-1 expressing ALCL, preferably ALK$^+$-ALCL, especially in NPM-ALK$^+$-ALCL.

The present invention is further illustrated by the following examples without being limited thereto.

EXAMPLES

Example 1

T-Cell Specific Deletion of JunB Together with cJun Significantly Increases the Survival Time of Mice Developing NPM-ALK Positive Lymphoma To investigate the role of junB and cjun in the formation of NPM-ALK positive lymphomas in vivo, we crossed transgenic mice carrying the human NPM-ALK fusion-tyrosine-kinase (FTK) under the control of the murine, T-cell specific, CD4-promotor with mice of the same background, independently expressing the CRE recombinase gene (CD4-CRE) that carried either floxed versions of the JunB gene or the cJun gene (JunB$^{f/f}$ or cJun$^{f/f}$) (Chiarle et al., Blood 101 (2003): 1919-1927; Wolfer et al., Nat. Immunol. 2 (2001), 235-241; Behrens et al., EMBO J. 21 (2002), 1782-1790). Using this approach we generated mice with T-cell specific expression of NPM-ALK and T-cell specific knockout of JunB and/or cJun. We established four mouse lines of interest. Mice carrying the transgene as well as a conditional knockout of JunB or cJun we termed NPM-ALK$^{\Delta c\text{-}Jun}$ or NPM-ALK$^{\Delta JunB}$, respectively. Mice carrying the transgene and a double knockout of JunB and cJun were termed NPM-ALK$^{\Delta Jun}$. We analyzed the survival times of the different mouse-strains using a Kaplan-Meier plot (FIG. 1a). While NPM-ALK$^{\Delta Jun}$ lived significantly longer than littermates without knockout (mean survival times 24+/−4.8 vs. 13.5+/−3.9 weeks), there were no significant differences in the survival times of NPM-ALK$^{\Delta JunB}$ or NPM-ALK$^{\Delta c\text{-}Jun}$ (12.8+/−4.7 and 11.3+/−3.2 weeks vs. 13.5+/−3.9 weeks) (FIG. 1a). Therefore, we decided to furthermore elucidate the differences of NPM-ALK and NPM-ALK$^{\Delta Jun}$ mice.

Figure 1B:
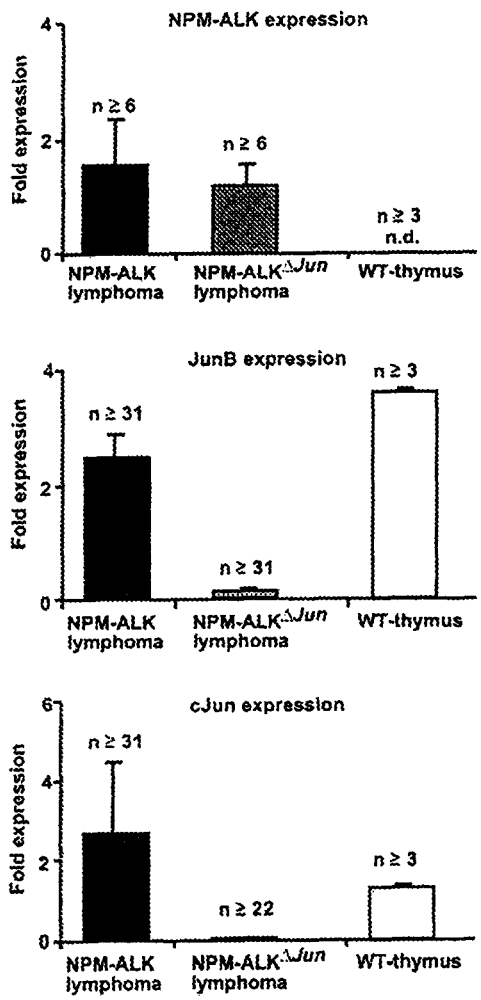

To ensure that CRE recombinase mediated gene deletions worked sufficiently and that NPM-ALK mRNA expression-levels were not influenced we investigated the levels of NPM-ALK, junB and cjun mRNA by qRT-PCR in the lymphomas of mice of the two genotypes mentioned above as well as in lymphatic tissue from control mice (thymus) (FIG. 1b). Thymus suited best as control tissue, since the tumors most frequently arise in this organ. NPM-ALK and NPM-ALK$^{\Delta Jun}$ lymphomas showed similar expression levels of NPM-ALK, while NPM-ALK was not expressed in the thymus of wild type mice.

JunB mRNA expression was slightly higher in the thymii of wild type mice than in the lymphomas of CD4 driven NPM-ALK expressing animals, however we could hardly detect any junB expression in lymphomas of NPM-ALK$^{\Delta Jun}$ mice. CJun mRNA expression was comparable in NPM-ALK mice's lymphomas and wild type mice's thymii, while expectedly there was no cjun expression in NPM-ALK$^{\Delta Jun}$ lymphomas. These data confirmed that the CRE recombinase based knockout strategy of junB and cjun yielded efficient abrogation of the corresponding mRNA levels.

Figure 1C:
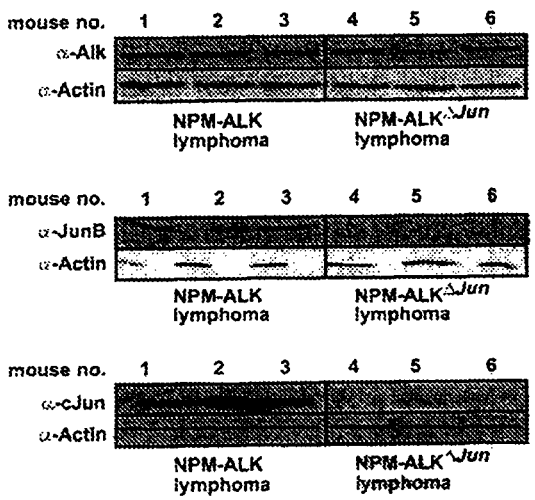

We subsequently analyzed the protein expression levels of NPM-ALK, junB and cjun in the lymphomas of NPM-ALK and NPM-ALK$^{\Delta Jun}$ mice (FIG. 1c). NPM-ALK protein expression was similar in both, NPM-ALK and NPM-ALK$^{\Delta Jun}$ mice, confirming that the knockout strategy did not influence NPM-ALK levels. JunB and cJun proteins were not detectable in NPM-ALK$^{\Delta Jun}$ lymphomas when compared to NPM-ALK mice, again confirming the efficiency of the CD-4 Cre mediated knockout strategy.

Example 2

Gene Expression Profiling in Human ALCL Patient Samples

Using Tissue Micro-arrays (TMA) technology (the Tissue Micro-arrays using paraffin embedded human patient samples of NPM-ALK positive and negative ALCL patients were provided from Dr. Ana Schmatz; Medical University Vienna) we analysed protein expression of ALCL patient samples. The JunB (Santa Cruz; sc-46), cJun (Santa Cruz; sc-1694) and PDGFRB (Cell Signaling; Cat. Nr. 3169) protein expression levels were elevated independent from the ALK (Dako; N1614) expression levels (FIG. 2 a and b).

PDGFRB is Highly Expressed in NPM-ALK, but not in NPM-ALK$^{\Delta Jun}$ Tumors

Figure 3A:
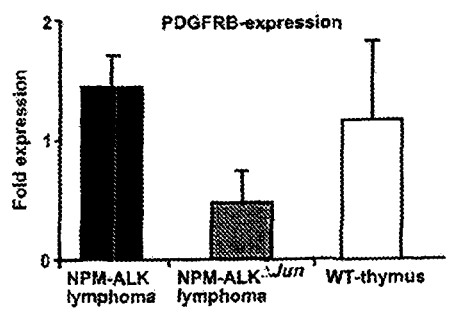
FIG. 3: PDGFRB mRNA levels were analyzed by qRT-PCR and were found to be reduced in NPM-ALK$^{\Delta Jun}$ tumors and wild type thymus compared to NPM-ALK tumors. (a) PDGFRB expression is highly expressed in mouse NPM-ALK tumors, but not in NPM-ALK$^{\Delta Jun}$ tumors and in wild type thymus. (b) Protein immunoblot quantification revealed that PDGFRB is actively expressed in most NPM-ALK, but not in NPM-ALK$^{\Delta Jun}$ tumors. (c) NPM-ALK mouse tumor cells produce PDGF and are able to stimulate PDGFRB expression and phosphorylation in mouse fibroblast cells. (d) IP for glycoproteins was performed, and protein levels of PDGFRB and p-PDGFRB was assessed by Western Blot. NPM-ALK induced lymphomas show reduced proliferation and increased apoptosis rates upon loss of cJun and JunB. (e) Ki-67 positive proliferation rates and TUNEL positive apoptosis rates of NPM-ALK and NPM-ALK$^{\Delta Jun}$ lymphomas were determined by immunofluorescence staining (right) and quantified by counting 10 HPF (left). In addition, Ki-67 positive proliferation rate was analyzed by IHC staining counting 10 HPF (High-Power Field) of each lymphoma (below). Proliferation rates in NPM-ALK$^{\Delta Jun}$ tumors were significantly reduced while the apoptosis rates were increased in comparison to NPM-ALK tumors. Cell cycle stains by FACS show that tumors of NPM-ALK$^{\Delta Jun}$ mice have significantly more cells in G1- and less in S-phase than tumors of NPM-ALK mice (f).
Figure 3B:
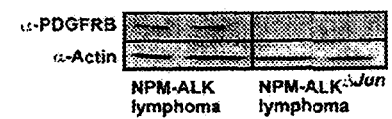
Figure 3C:
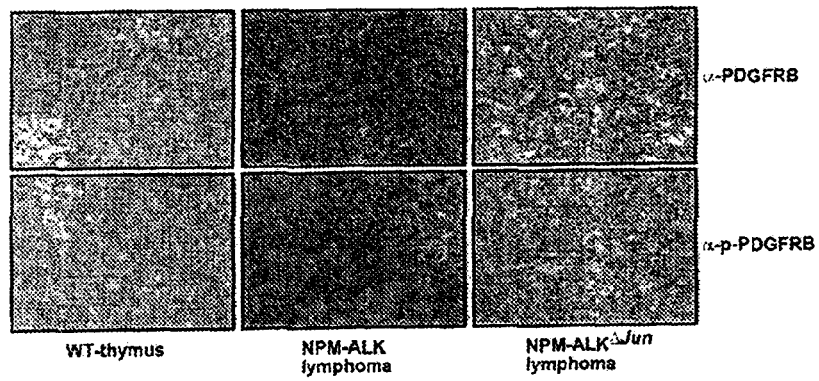
Figure 3D:
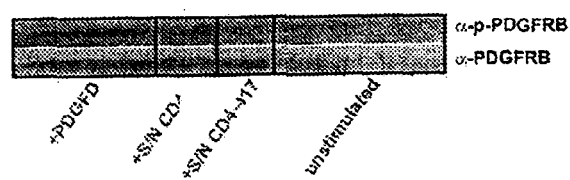
Figure 3E:
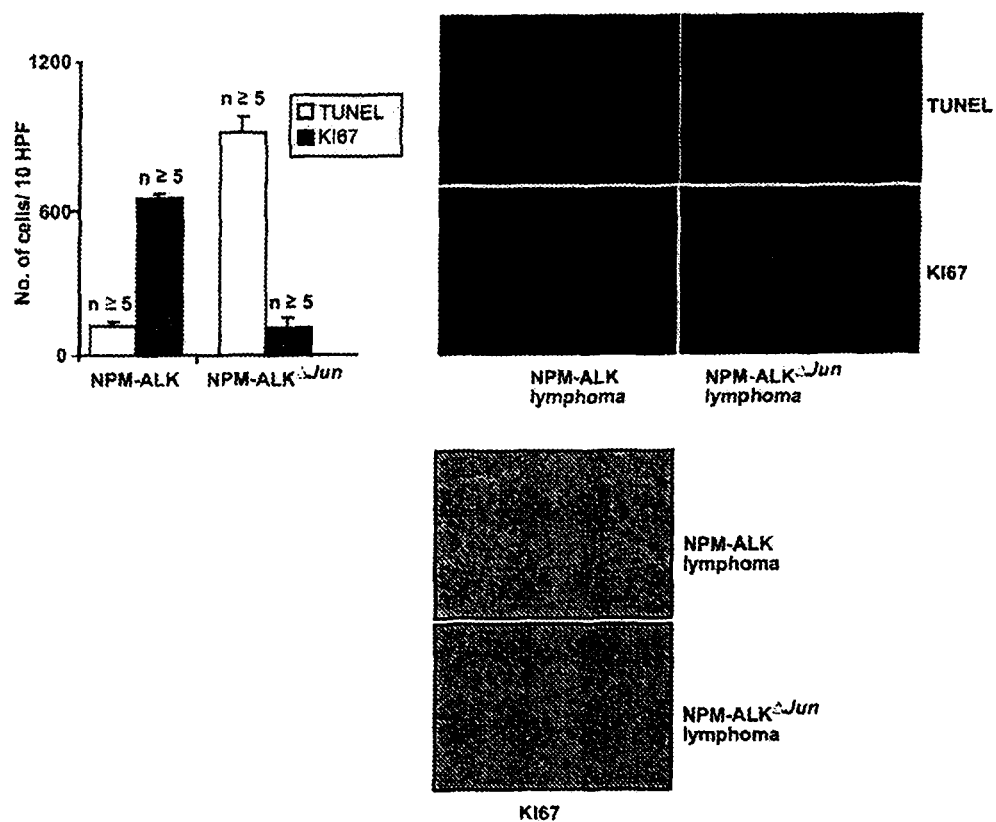

We analyzed the murine as well as human NPM-ALK lymphoma tumor samples for the RNA expression of PDGFRB. We found that PDGFRB expression is similar in lymphomas of NPM-ALK$^{\Delta Jun}$ mice compared to NPM-ALK mice using qRT-PCR. In wild type thymii, the expression is 50% lower than in the tumors (FIG. 3a). While the tumors of NPM-ALK mice are positive for PDGFRB, we show that PDGFRB protein expression is completely abolished in NPM-ALK$^{\Delta Jun}$ mice (FIG. 3b). We also analyzed PDGFRB expression in NPM-ALK versus NPM-ALK$^{\Delta Jun}$ lymphomas and livers by IHC. PDGFRB expression is high in NPM-ALK lymphomas, whereas NPM-ALK$^{\Delta Jun}$ mice do not express PDGFRB (FIG. 3c and data not shown). Fibroblast cells were starved over night in serum free medium, then PDGFD (positive control), serum of a NPM-ALK positive mouse tumor cell lines (CD4-4 or CD4-417, respectively, G. Inghirami; University of Turin) or serum free medium was added to the fibroblast cells. Immunoprecipitation for glycoproteins was performed, and protein levels of PDGFRB and p-PDGFRB (Cell Signaling; Cat. Nr. 3124) was assessed by Western Blot analysis of an autostimulatory loop in murine NPM-ALK lymphomas. NPM-ALK mouse tumor cells produce PDGF and are able to stimulate PDGFRB expression and phosphorylation in mouse fibroblast cells in an autostimulatory manner (FIG. 3d).

Example 3

Tumors of NPM-ALK$^{\Delta Jun}$ Mice Show Reduced Proliferation and Increased Apoptotic Markers As the NPM-ALK lymphomas in the mice are extremely aggressive, it is not possible to analyze these earlier stages of tumor formation directly; the mice show no sign of illness until a few hours before death by suffocation, and the survival time varies greatly from about 8 up to about 30 weeks (see FIG. 1a). We therefore analyzed proliferation and apoptosis rates at the time of death in lymphomas via immunofluorescence and immunohistochemical staining for Ki-67 (Novocastra; NLC-Ki67p) and TUNEL (Chemicon; S7111) assays, respectively (FIG. 2e). We found that the staining using the proliferation marker Ki-67 in tumors from double knockout animals was strongly reduced, while the apoptotic rate, as measured by TUNEL staining was increased in NPM-ALK$^{\Delta Jun}$ mice. Using flow cytometry we analyzed the cell cycle parameters of NPM-ALK versus NPM-ALK$^{\Delta Jun}$ lymphoma cells. The latter remained significantly longer in G-phase but much shorter in S-phase (FIG. 3f).

Example 4

PDGFRB is a Novel Target of JunB and cJun

Figure 4A:
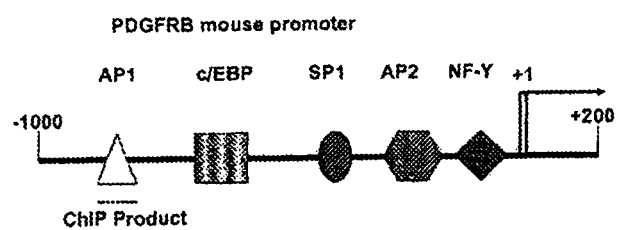
FIG. 4: PDGFRB is a direct target of JunB and cJun. (a) Highly conserved AP-1 site of the PDGFRB in several species as indicated (Mouse=SEQ ID NO: 9; Rat=SEQ ID NO: 10; Human=SEQ ID NO: 11; Orangutan=SEQ ID NO: 12; Dog=SEQ ID NO: 13; Horse=SEQ ID NO: 14; Opossum=SEQ ID NO: 15; Chicken=SEQ ID NO: 16). (b) ChIP analysis and diagram of the mouse PDGFRB-promoter. In the diagram, the site of the ChIP-product and binding sites of AP-1, c/EBP, SP1, AP-2 and NF-Y are indicated. ChIP analysis was performed with a NPM-ALK mouse tumor cell line. Cell extracts without antibodies serve as negative controls. As a positive control histone H3 Abs were used. QRT PCR with Primers specific for the AP-1 site in the PDGFRB promoter was performed with the RNA extracted after the ChIP. JunB and cJun both bound to the PDGFRB promoter sequence. (c) Luciferase constructs were made containing (PDGFRB-luc) or lacking (PDGFRB (w/o AP-1.site)-luc) AP-1 site. P-GL3-luc is a vector containing firefly-luciferase, while p-vec and p-PDGFRB-luc is an empty vector and PDGFRB promoter with luciferase. P-cJun, p-JunB and p-PDGFRB-luc indicate vectors containing cJun and JunB cDNA (P. Vesely) as well as the PDGFRB promoter with luciferase, respectively. P-vec+p-PDGFRB(w/o AP-1 site)-luc indicates the empty vector and the PDGFRB promoter with deleted AP-1 site. Only p-cJun, p-JunB and p-PDGFRB-luc together create a strong signal, confirming specific binding of cJun and JunB to the PDGFRB AP-1 site. (d) EMSA probes were designed containing the correct AP-1 sequences or mutated versions (labeled "mut") with two bases exchanged (AP15'=SEQ ID NO: 17; AP13'=SEQ ID NO: 18; AP1mut5'=SEQ ID NO: 19; AP1mut3'=SEQ ID NO: 20; PDGFRBAP15=SEQ ID NO: 21; PDGFRBAP13=SEQ ID NO: 22; PDGFRBAP1mut5=SEQ ID NO: 23; PDGFRBAP1mut3=SEQ ID NO: 24). EMSAs were performed using NPM-ALK positive tumor cell extracts and probes for a control AP-1 site, the PDGFRB AP-1-site and the mutated versions of these sequences. Both probes for the control AP-1 site and the PDGFRB AP-1, but not the mutated probes give a strong signal. In addition, supershift assays taking advantage of the PDGFRB AP-1 site and antibodies specific for JunB and cJun were performed. The AP-1 band clearly shifts upon Ab binding, confirming specific binding of the respective Jun-antibodies.
Figure 4B:
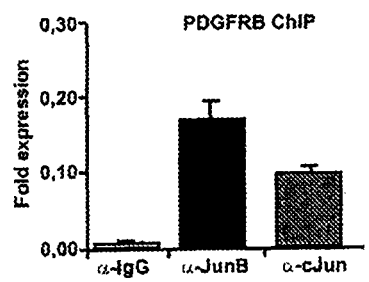

Next, we analyzed the regulation of PDGFRB by JunB and cJun. Using the "UCSC Genome Browser on Mouse July 2007 Assembly" and Math Inspector (Kent et al., Genome Res. 12 (2002): 996-1006; Cartharius et al., Bioinformatics 21 (2005), 2933-2942) we were able to identify an AP-1 consensus sequence within the PDGFR promoter from −269 bp to −263 by upstream from the transcriptional start site, which is highly conserved across several mammalian species (FIG. 4a). This in silico finding lead us to the assumption that the PDGFRB promoter might be regulated via AP-1 factors, and that PDGFRB possibly might be a novel and as yet unknown AP-1 target gene. To test this hypothesis, we performed Chromatine Immunopreciptiation (ChIP) analysis using a murine CD4-NPM-ALK cell line (Line 417) (G. Inghirami, University of Turin). This cell line was derived from primary tumors of the same NPM-ALK mice we use. The Ch IP was performed with an anti-JunB as well as with an anti cJun antibody, and the resulting material was analyzed by qRT-PCR with primers binding at the putative AP-1 binding site of the PDGFRB-promoter (see figure legends). We were able to show that JunB as well as cJun bind to this AP-1 site, suggesting PDGFRB as an AP-1 target gene (FIG. 4b).

Figure 4C:
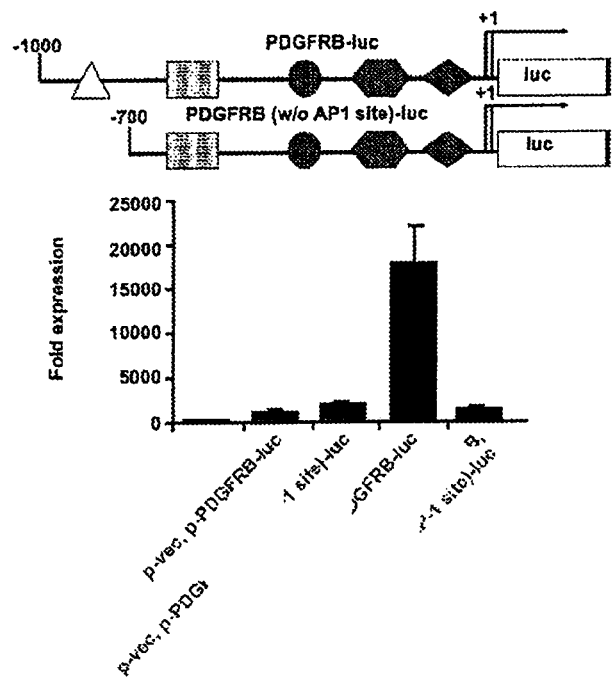

To further confirm these results, we performed Luciferase Reporter Gene Assays using two different PDGFRB promoter luciferase constructs. In both cases we cloned part of the murine PDGFRB promoter into the multiple cloning site of the pGL3 basic promoter. In the first case (PDGFRB-Luc) we used a fragment including the AP-1 consensus site from −269 bp to −263 bp upstream from the transcriptional start site and in the second case (PDGFRBΔ-Luc) we excluded this region (see figure legends). Co-transfection of cJun and JunB expressing vectors with the PDGFRB-Luc promoter construct containing the AP-1 binding site resulted in strong luciferase activation, whereas the PDGFRBΔ-Luc construct lacking the AP-1 binding site could not be induced by cJun and JunB. These data indicate that the combination of cJun and JunB strongly induces the PDGFRB promoter via its AP-1 site (FIG. 4c).

Figure 4D:
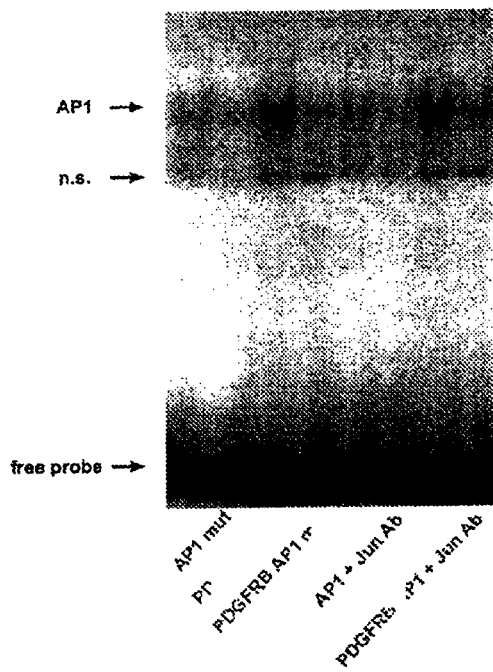
Figure 5:
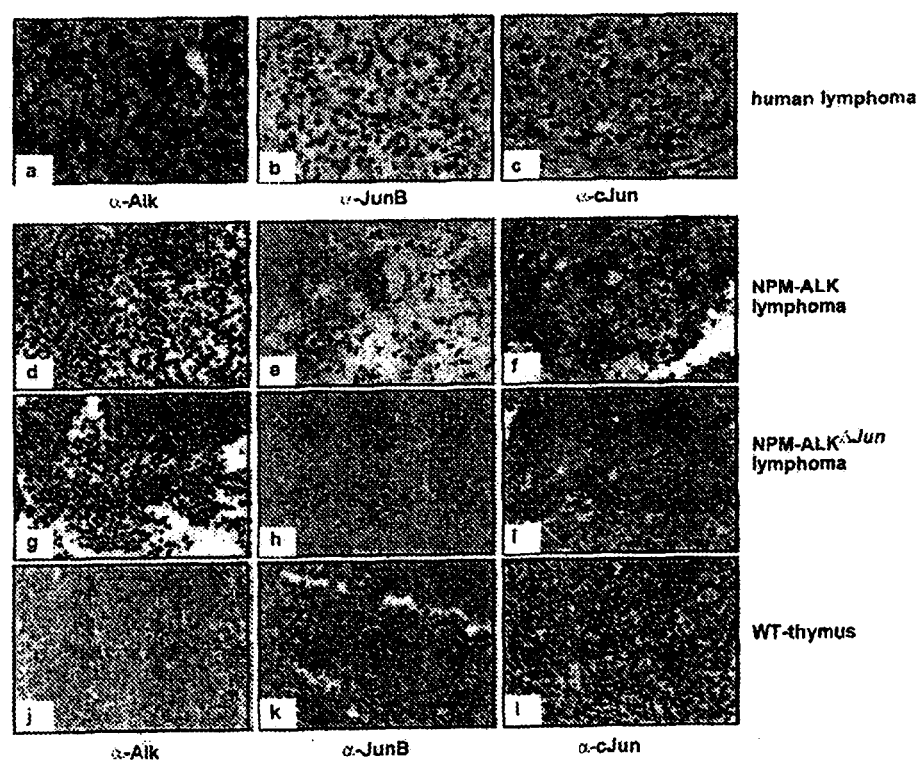
FIG. 5: Analysis of NPM-ALK, JunB and cJun protein levels in human and mouse lymphomas and respective controls by IHC. While NPM-ALK levels are similar in human NPM-ALK positive lymphomas, NPM-ALK and NPM-ALK$^{\Delta Jun}$ mouse tumors, no NPM-ALK expression is detectable in wild type lymph nodes. JunB is expressed in human lymphomas as well as the NPM-ALK positive murine lymphomas, but absent in NPM-ALK$^{\Delta Jun}$ tumors and wild type lymph nodes. cJun is expressed in all tissues except for NPM-ALK$^{\Delta Jun}$ tumors.
Figure 6C:
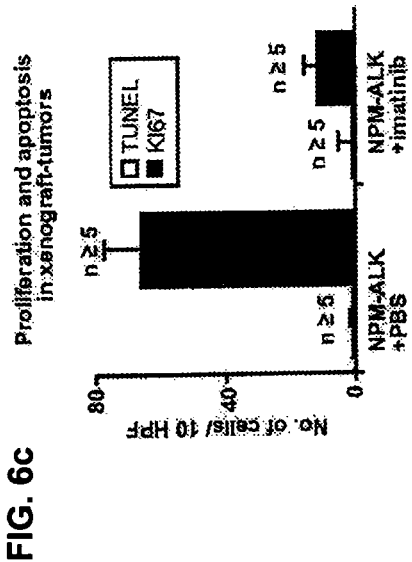
FIG. 6: Inhibition of PDGFRB by using specific bockage with imatinib leads to reduced cell numbers and increased apoptosis rates in vitro and reduced tumor size as well as reduced proliferation rates in vivo resulting in a more than 90% tumor size reduction. (a) Tumor weight was drastically reduced after 5 days of treatment with imatinib in comparison to untreated control tumors. (b) Direct size comparison of tumors of treated versus an untreated mice show the severe reduction in tumor size of the imatinib-treated mice. (c) Proliferation and apoptosis rates in the tumors of the xenografted mice were assessed by Ki-67 and TUNEL by IHC staining, respectively. Proliferation was severely reduced in imatinib treated mice, while there was no significant difference in apoptosis rates. (d) Western Blot analysis reveals a higher PDGFRB-expression in the tumors of imatinib treated xenografted mice compared to untreated controls.
Figure 6A:
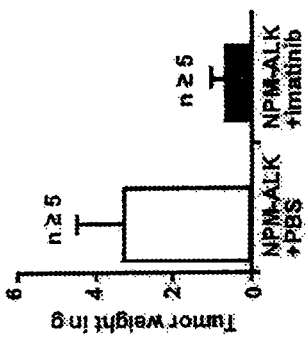
Figure 6B:
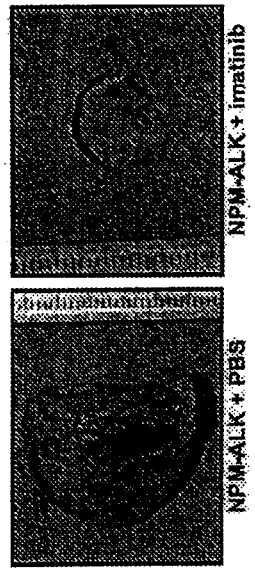
Figure 6D:
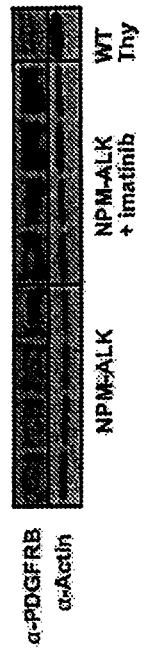
Figure 7A:
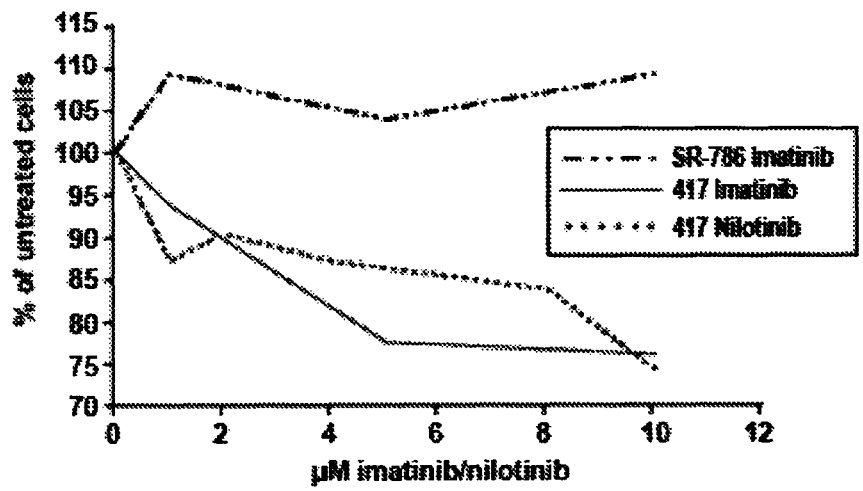
FIG. 7: Inhibition of PDGFRB by using specific bockage with nilotinib leads to reduced cell numbers in vitro and reduced tumor size as in vivo resulting in a more than 59% tumor size reduction. (a) antiproliferative effect: Treatment with nilotinib and imatinib leads to a dose dependent reduction in cell number in PDGFRB expressing NPM-ALK expressing cells (cell line 417; G. Inghirami; University of Turin), while proliferation rates in PDGFRB negative SR-786 (G. Egger; MUW) cell line are unaffected. (b) Tumor weight was drastically reduced after 6 days of treatment with nilotinib in comparison to untreated control tumors.
Figure 7B:
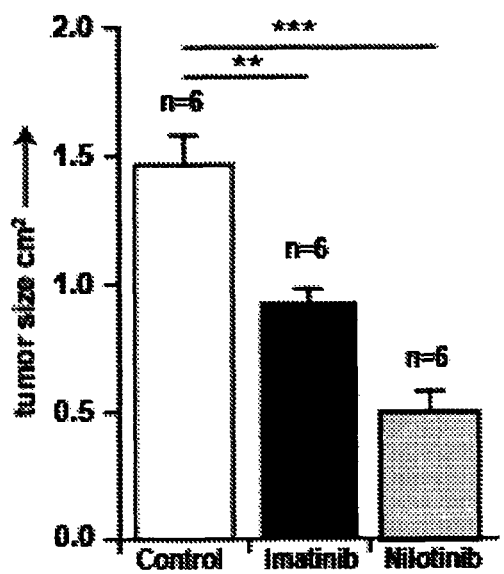
Figure 8A:
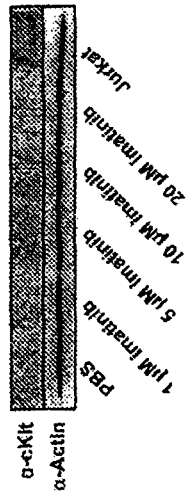
FIG. 8: Western Blot analysis of PDGFRB protein expression in SR-786 and 417 cell lines. (a) Only cell line 417 is positive for PDGFRB. (b) Western Blot analysis reveals that c-kit is not expressed in any of the analyzed NPM-ALK lymphoma samples. (c) Treatment with imatinib in vitro leads to a dose dependent apoptosis in 417 cells, while SR-786 cells are unaffected. Apoptosis was measured by Alamar Blue assay. While cell line 417 shows high apoptosis three days after treatment with 20 μM imatinib, cell line SR-786 was unaffected.
Figure 8B:
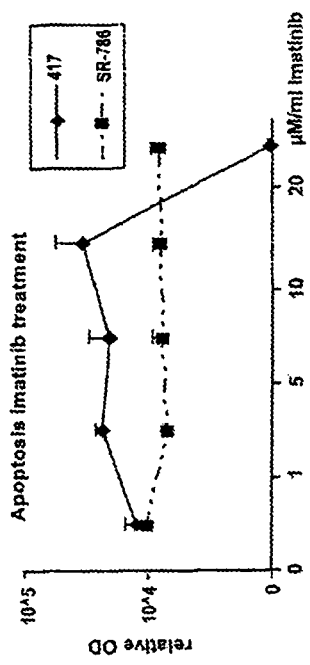
Figure 8C:
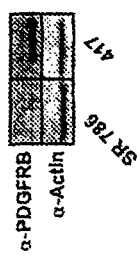

Finally, we analyzed the PDGFRB AP-1 site in NPM-ALK mouse tumor protein extracts by EMSA. When tumor extracts were incubated with a probe containing the TPA (1 2-O-tetradecanoylphorbol-13-acetate)-response element (TRE) a strong band shift was observed by EMSA. However, a mutated TRE sequence abolished this effect (FIG. 4d). Moreover, pre-incubation of the tumor extract with antibodies specific for cjun and junB lead to a near complete loss of the shifted band. These findings however, indicate PDGFRB as a novel AP-1 target gene.

Using immunohistochemistry (IHC), we assessed the expression levels of NPM-ALK, junB and cjun in human ALCLs, NPM-ALK and NPM-ALK$^{\Delta Jun}$ murine lymphomas as well as in lymph nodes from isogenic wild type animals. NPM-ALK staining was comparable in all lymphoma samples, while it was not detectable in the wild type lymph nodes. Human as well as mouse NPM-ALK positive ALCL lymphomas show high expression of JunB and cJun, whereas NPM-ALK$^{\Delta Jun}$ mice express no JunB nor cJun. However, wild lymphatic tissue type i.e. thymus expresses JunB and cJun at a low level (supplementary FIG. 1).

Example 5

Treatment of Murine NPM-ALK Tumor Cells with Imatinib or Nilotinib Leads to Reduced Proliferation and Increased Apoptosis In Vitro To investigate the role of PDGFRB for NPM-ALK tumorigenesis, we treated cells of the murine NPM-ALK and PDGFRB positive cell line 417 and the human NPM-ALK positive and PDGFRB negative cell line SR-786 (supplementary FIG. 3a) [G. Egger, Medical University Vienna] with different concentrations of the tyrosine kinase inhibitors imatinib-mesylate (imatinib) and nilotinib. Cells were cultured for three days in RPMI medium and subsequently analysis for cell number and apoptosis rates was performed. Cell number was increasingly impaired in cell line 417 as concentrations of imatinib increased. SR-786 cells however were completely unaffected.

Example 6

Treatment of Murine NPM-ALK Tumors with Imatinib and Nilotinib In Vivo Leads to Reduction in Tumor Size To test the effects of imatinib and nilotinib as well in vivo, we established a murine xenograft model, by injecting cells of the murine NPM-ALK positive cell line CD4-417 into the right flank of 6 weeks old SCID (severe combined immunodeficiency) mice. Four weeks after injection, solid tumors developed and mice were treated daily with 300 mg/kg/day imatinib or 75 mg/kg/day nilotinib, respectively by gavage.

Figures 2A, 2B:
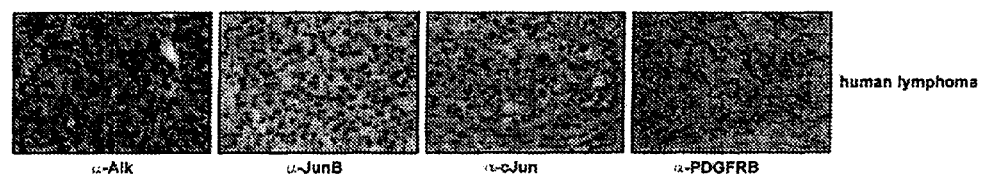
FIG. 2: Immunhistochemistry analysis of NPM-ALK positive versus NPM-ALK negative human ALCL patient samples. (a) Immunohistochemistry analysis of Tissue Microarray from ALCL patients (TMA) shows concomitant expression of ALK, JunB, cJun and PDGFRB in NPM-ALK positive nodal and cutanous lymphomas (n=29). (b) Table of NPM-ALK positive versus NPM-ALK negative human ALCL patient samples. IHC analysis using Abs against PDGFRB, cJun and JunB and ALK.
Figure 3F:
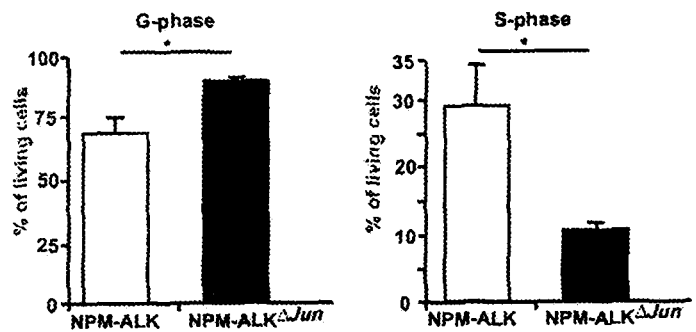

After a course of seven days, mice treated with imatinib showed complete remission or greatly reduced tumors (untreated mice: 2.7 g, treated mice 0.5 g) (supplementary FIGS. 2a and b; supplementary FIG. 3b). Moreover, in accordance to the tumor phenotype observed in NPM-ALK$^{\Delta Jun}$ mice, treatment of the grafted tumors with imatinib lead to reduced proliferation and slightly enhanced apoptosic rates, as measured by Ki-67 and TUNEL Immunofluorescence staining (supplementary FIG. 2c). PDGFRB protein expression is upregulated in imatinib treated mice. This is probably a counter action to the blockage of PDGFRB-phosphorylation by imatinib (supplementary FIG. 2d). These data are supporting that imatinib and nilotinib block PDGFRB in ALCL.

Example 7

Treatment of Murine NPM-ALK Tumor Cells with Imatinib or Nilotinib Leads to Reduced Proliferation and Increased Apoptosis In Vitro Apoptosis rates were measured by Alamar Blue assays. The active ingredient of Alamar Blue is resazurin, a non-fluorescent dark blue indicator dye. It is able to permeate cells and is converted to resorufin, a fluorescent, bright red dye, in a reduction reaction by living (metabolically active) cells. The produced fluorescence is proportional to the number of metabolically active cells.

We incubated SR-786 and 417 cells treated with 0-20 μM imatinib with Alamar Blue for one hour at 37 degrees Celsius. The SR-786 cells were able to convert the resazurin to resorufin at a comparable rate, regardless of imatinib concentrations in the medium. 417 cells treated with 0-10 μM responded similar to SR-786 cells. 417 cells treated with 20 μM imatinib though were not able to induce the color change from dark blue to red, indicating that few living cells were present. Similar to the proliferation rates, apoptosis was unaffected in SR-786 cells, while in 417 cells apoptosis strongly increased at 20 μM/ml imatinib (supplementary FIG. 4c). These results show that the mouse cells 417 strongly react to imatinib and nilotinib, while the human SR-786 cells remain unaffected, proving that the reaction of the 417 cells is not due to toxic doses of imatinib. The reason for the different response of the cell lines is probably due to the lack of PDGFRB expression in the SR-786 cells. As most human NPM-ALK positive lymphomas, as well as the mouse tumors and cell line 417 are positive for PDGFRB, it is likely that the human cell line has originally expressed PDGFRB expression and lost it due to long time culture. Cells in culture do not need to induce neovasculature to be supplied with nourishment, so for cells in longterm-culture it would make sense to reduce expression of a factor like PDGFRB, which is mainly involved in building blood vessels. Therefore, the assumption that imatinib treatment in humans would not work because it does not inhibit NPM-ALK itself and because it does not affect human NPM-ALK positive cells is not valid.

To exclude the possibility of imatinib acting through inhibition of c-kit, Western Blot Analysis for c-kit (Dako, A4502) was performed. As expected, c-kit was not expressed in cell line 417 (supplementary FIGS. 4a and b).

The invention claimed is:

1. A method of treating a patient with anaplastic lymphoma kinase+(ALK+)-anaplastic large cell lymphoma (ALCL) and susceptible to a cell proliferative disorder comprising: obtaining a platelent-derived growth factor receptor beta (PDGFRbeta) antagonist; and administering the PDGFRbeta antagonist to the patient.

2. The method of claim 1, wherein the patient has nucleophosmin-anaplastic lymphoma kinase+(NPM-ALK+)-ALCL.

3. The method of claim 1, wherein the patient is in relapse.

4. The method of claim 1, wherein the patient is in first line therapy.

5. The method of claim 1, wherein the PDGFRbeta antagonist is nilotinib, imatinib, dasatinib, axitinib, sunitinib, or toceranib.

6. The method of claim 1, further defined as being a prophylactic treatment.

7. The method of claim 1, further defined as being a therapeutic treatment.

8. The method of claim 1, wherein the PDGFRbeta antagonist is administered locally or systemically.

9. The method of claim 1, wherein the PDGFRbeta antagonist is administered orally.

10. The method of claim 9, wherein the PDGFRbeta antagonist is administered at a dose ranging from 0.001 mg/kg/day to about 100 mg/kg/day.

11. The method of claim 10, wherein the PDGFRbeta antagonist is administered in combination with chemotherapy and/or radiation therapy.

12. The method of claim 1, further comprising determining whether the ALCL cells of the patient express activator protein-1 (AP-1) prior to administering the PDGFRbeta antagonist to the patient.

13. The method of claim 1, further comprising determining whether the ALCL cells of the patient express activator protein-1 (AP-1) after administering the PDGFRbeta antagonist to the patient.

* * * * *

UNITED STATES PATENT AND TRADEMARK OFFICE
CERTIFICATE OF CORRECTION

PATENT NO. : 8,933,037 B2  
APPLICATION NO. : 13/498827  
DATED : January 13, 2015  
INVENTOR(S) : Lukas Kenner and Daniela Laimer Page 1 of 1

It is certified that error appears in the above-identified patent and that said Letters Patent is hereby corrected as shown below:

Title Page 2, Item (56) References Cited, Other Publications

Add the following reference:

-- ROSKOSKI et al: "Sunitinib: A VEGF and PDGF receptor protein kinase and angiogenesis inhibitor,: Biochemical and Biophysical Research Communications, vol. 356, pp. 323-328, 2007. --

Signed and Sealed this  
Fifth Day of May, 2015

Michelle K. Lee  
*Director of the United States Patent and Trademark Office*